United States Patent [19]

Aoyama et al.

[11] Patent Number: 5,557,019

[45] Date of Patent: Sep. 17, 1996

[54] METHOD FOR PREPARING DICHLORODECAFLUOROPENTANE AND DECAFLUOROPENTANE

[75] Inventors: Hirokazu Aoyama; Satoru Kohno; Satoshi Koyama, all of Settsu, Japan

[73] Assignee: Daikin Industries Ltd., Osaka, Japan

[21] Appl. No.: 290,776

[22] PCT Filed: Feb. 22, 1993

[86] PCT No.: PCT/JP93/00214

§ 371 Date: Aug. 24, 1994

§ 102(e) Date: Aug. 24, 1994

[87] PCT Pub. No.: WO93/16973

PCT Pub. Date: Sep. 2, 1993

[30] Foreign Application Priority Data

Feb. 28, 1992 [JP] Japan .................................. 4-043043
May 22, 1992 [JP] Japan .................................. 4-155748

[51] Int. Cl.$^6$ ...................... C07C 17/093; C07C 17/278; C07C 19/01; C07C 19/08

[52] U.S. Cl. ........................... 570/176; 570/134; 570/172

[58] Field of Search ....................... 570/134, 172, 570/176

[56] References Cited

U.S. PATENT DOCUMENTS

| 2,920,112 | 1/1960 | Larsen ...................................... 570/176 |
| 2,942,036 | 6/1960 | Smith et al. ............................... 570/176 |
| 4,740,640 | 4/1988 | Boutevin et al. ........................... 570/172 |
| 4,935,558 | 6/1990 | Krespan et al. ............................ 570/176 |
| 5,068,473 | 11/1991 | Kellner et al. ............................ 570/176 |
| 5,268,122 | 12/1993 | Rao et al. ................................. 570/134 |
| 5,434,321 | 7/1995 | Ohnishi et al. ............................ 570/172 |

FOREIGN PATENT DOCUMENTS

| 308923 | 3/1989 | European Pat. Off. ............... 570/176 |
| 222038 | 12/1983 | Japan .................................... 570/134 |
| 193841 | 7/1992 | Japan .................................... 570/172 |
| 124987 | 5/1993 | Japan .................................... 570/176 |

*Primary Examiner*—Joseph E. Evans
*Attorney, Agent, or Firm*—Armstrong, Westerman, Hattori, McLeland & Naughton

[57] ABSTRACT

A new 3,3-dichloro-1,1,1,2,2,4,4,5,5,5-decafluoropentane as a precursor of alternatives of refrigerants, etc.

A method to obtain the target products at high yield and high selectivity by reacting tetrafluoroethylene and difluorodichloromethane under the Lewis acid catalyst to produce the new compound and an economical method in a continuous reaction state.

A production method of 1,1,1,2,2,4,4,5,5,5-decafluoropentane at high yield by reducing 3,3-dichloro-1,1,1,2,2,4,4,5,5,5-decafluoropentane.

7 Claims, No Drawings

METHOD FOR PREPARING DICHLORODECAFLUOROPENTANE AND DECAFLUOROPENTANE

This application is a 371 of PCT/JP93/00214 filed Feb. 22, 1993, and published as WO93/16973 Sep. 2, 1993.

APPLICABLE FIELD TO THE INDUSTRY

The present invention relates to a production method of 1,1,1,2,2,4,4,5,5,5-decafluoropentane (HFC-43-10 mcf) as an alternative compound of CFC and HCFC used for refrigerants, foaming agents, and cleaning agents, and its intermediate product (precursor) for the production method or 3,3-dichloro-1,1,1,2,2,4,4,5,5,5-decafluoropentane (and 2,2-dichloro-1,1,1,3,3,4,4,5,5,5-decafluoropentane) very effective as an intermediate of a monomer during production of macromolecular fluorocompounds and many intermediate products of fluorocompounds.

PRIOR ART

Decafluoropentane can be as an alternative (alternative freon) of CFC and HCFC used for refrigerants, foaming agents, and cleaning agents. In particular, HFC-43-10 mcf, like conventionally used freon, is expected to be applied for foam agents, refrigerants, and cleaning agents, and has an advantage not to destroy the ozone layer in the stratosphere because of no chlorine.

However, a production method of HFC-43-10 mcf has not been completely known in the past. Raw materials to synthesize such decafluoropentane have not been studied.

OBJECT OF THE INVENTION

The object of the invention is to provide a new compound to synthesize the said decafluoropentane and a production method to give the said new product at high yield and high selectivity.

Further object of the invention is to provide a production method of HFC-43-10 mcf at high yield and industrial scale economically.

COMPOSITION OF THE INVENTION

The first invention of the present application relates to 3,3-dichloro- 1,1,1,2,2,4,4,5,5,5-decafluoropentane (and 2,2-dichloro- 1,1,1,3,3,4,4,5,5,5-decafluoropentane).

The second invention of the present application relates to a production method of 3,3-dichloro-1,1,1,2,2,4,4,5,5,5-decafluoropentane (and 2,2-dichloro-1,1,1,3,3,4,4,5,5,5-decafluoropentane) characterized by reaction of tetrafluoroethylene and difluorodichloromethane under Lewis acid catalyst.

In this case, it is desirable to react the reactants contacting Lewis acid at gaseous and liquid phases at −20° to +100° C.

2,2-dichloro-1,1,1,3,3,4,4,5,5,5-decafluoropentane and 3,3-dichloro- 1,1,1,2,2,4,4,5,5,5-decafluoropentane related to the above first invention are new products shown by the following chemical formulas:

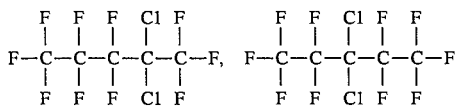

These new products are very useful, as they are, as intermediates of monomers to produce macromolecular fluorocompounds and many intermediate compounds of fluorocompounds, and they can be converted by reduction into decafluoropentane, as shown by the following formulas, usable for alternatives of CFC and HCFC (alternative freon) applying for refrigerants, foaming agents, and cleaning agents.

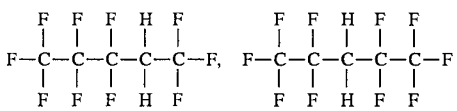

Referring to the first invention, 2,2-dichloro- 1,1,1,3,3,4,4,5,5,5-decafluoropentane and 3,3-dichloro- 1,1,1,2,2,4,4,5,5-decafluoropentane are new materials with boiling point of 90° C. and are very useful as described above, but their effective production methods are unknown.

However, the present inventors studied hard the effective production method of 2,2-dichloro-1,1,1,3,3,4,4,5,5,5-decafluoropentane and 3,3-dichloro-1,1,1,2,2,4,4,5,5,5-decafluoropentane and found that tetrafluoroethylene and difluorodichloromethane react under the presence of Lewis acid catalysts as shown below to produce 2,2-dichloro-1,1,1,3,3,4,4,5,5,5,-decafluoropentane and 3,3-dichloro-1,1,1,2,2,4,4,5,5,5-decafluoropentane at high yield to arrive at the production method of the said second invention.

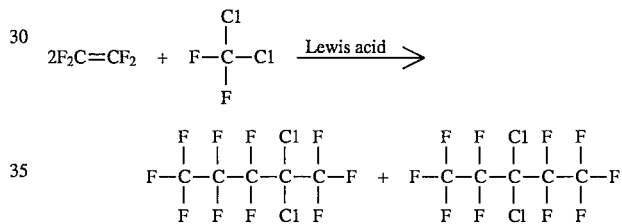

The Lewis acid catalyst used for the invention may be selected from titanium tetrachloride anhydride, zirconium tetrachloride anhydride, tin tetrachloride anhydride, antimony pentachloride anhydride, zinc chloride anhydride, iron chloride anhydride, aluminum bromide anhydride, and boron trifluoride as well as aluminum chloride anhydride.

The catalyst may be selected from metallic chlorofluoride catalyst of aluminum-, zirconium-and titanium-chlorofluoride shown by the following formulas.

Formulas: $AlCl_xF_y$, $ZrCl_pF_q$, or $TiCl_pF_q$ (In the formula, x and y are figures meeting $x+y=3$, $0<x<3$, $0<y<3$, and p and q are figures satisfying $p+q=4$, $0<p<4$, and $0<q<4$).

Among the Lewis acids above, the most favorable catalyst is aluminum chloride anhydride, titanium tetrachloride anhydride, zirconium tetrachloride anhydride; and aluminum chlorofluoride, zirconium chlorofluoride, and titanium chlorofluoride shown by the formulas: $AlCl_xF_y$, $ZrCl_pF_q$, and $TiCl_pF_q$.

Aluminum chloride anhydride, zirconium tetrachloride anhydride, titanium tetrachloride anhydride used for the invention may be particle, powder and liquid state available in the commercial market.

The said aluminum chlorofluoride, zirconium chlorofluoride, and titanium chlorofluoride can be produced by reacting commercially available aluminum chloride anhydride, zirconium tetrachloride anhydride, and titanium tetrachloride anhydride with hydrogen fluoride, fluoric acid, fluorohydrocarbon, hydrochlorofluorocarbon or chlorofluoro hydrocarbon with the number of carbons not more than four (preferably not more than two), for example, trifluoromethane, tetrafluoroethane, chlorodifluoromethane, dichlorofluoromethane, trifluorodichloroethane, trifluorochloromethane, dichlorodifluoromethane, trichlorofluoromethane, difluorotetrachloroethane, and trifluorotrichloroethane. At this time, each chemical may be used either alone or mixed each other, or mixed with chlorohydrocarbon on the situation.

A temperature condition of this reaction may be 0° to 120° C., favorably ranging 0° to 100° C., and may be effected under contact with aluminum chloride anhydride, zirconium tetrachloride anhydride and titanium tetrachloride anhydride in liquid state or by passing gas.

Referring to the method of the invention, the reaction state can be variously selected and can be selected from the following methods; (1) a method to charge specified all volume of the catalyst and raw materials of difluorodichloromethane and tetrafluoroethylene in a pressurized reaction vessel to react, (2) a method to charge tetrafluoroethylene as gas state after charging the specified volume of catalyst and another raw material of difluorodichloromethane, (3) a method to charge difluorodichloromethane and tetrafluoroethylene at the specified mole ratio into the catalyst dispersed in solvent under pressurized or atmospheric pressure conditions, or (4) a gaseous reaction to pass difluorodichloromethane and tetrafluoroethylene at the specified mole ratio through the reaction tube filled with the catalyst.

The reaction is fully effected even without solvent, but may use solvent if needed. Any solvent is acceptable if not deactivate the catalyst, perfluorohexane and dichloropentafluoropropane and so on can be used, but considering subsequent separation and purification processes difluorodichloromethane as one of raw materials, or products of 2,2-dichloro-1,1,1,3,3,4,4,5,5,5-decafluoropentane and 3,3-dichloro-1,1,1,2,2,4,4,5,5,5-decafluoropentane are preferable to be used as solvent.

A mole ratio of difluorodichloromethane and tetrafluoroethylene for raw materials can be largely varied, however, a ratio of 1:2 may be usually applied, but changing mole ratio gives no merit.

The reaction pressure is not specifically defined, but it ranges normally 0 to 30 kg/cm$^2$G, preferably 0 to 20 kg/cm$^2$G.

The reaction temperature may be normally at −20° to +100° C., preferably −20° to +60° C. The reaction temperature if exceeds 100° C. causes to increase reaction byproduct to lower the selectivity of the target products of 2,2-dichloro-1,1,1,3,3,4,4,5,5,5-decafluoropentane and 3,3-dichloro-1,1,1,2,2,4,4,5,5,5-decafluoropentane. On the other hand, the reaction temperature lower than −20° C. causes to remarkably delay the reaction speed not practically.

Initial raw materials, difluorodichloromethane and tetrafluoroethylene used for the present invention are both industrially produced now. The Lewis acid such as aluminum chloride anhydride available from the market can be used as it is.

In addition, the said synthesized 2,2-dichloro-1,1,1,3,3,4,4,5,5,5-decafluoropentane and 3,3-dichloro-1,1,1,2,2,4,4,5,5,5-decafluoropentane if reduced with hydrogen can be converted to 1,1,1,3,3,4,4,5,5,5-decafluoropentane and 1,1,1,2,2,4,4,5,5,5-decafluoropentane (HFC-43-10 mcf) applied for alternatives of CFC and HCFC used for refrigerants, foaming agents, and cleaning agents. The hydrogen reduction method is not specified so that, for example, a gaseous phase reduction method at 100° to 300° C. using alumina carrying Pd of 0.5% as a catalyst or a liquid phase reduction with zinc may be applied.

According to the invention, especially reducing 3,3-dichloro-1,1,1,2,2,4,4,5,5,5-decafluoropentane can produce HFC-43-10 mcf at high yield.

Referring to the method of the invention, 3,3-dichloro-1,1,1,2,2,4,4,5,5,5-decafluoropentane used as the raw material can be easily produced by adding 1,1-dichlorohexafluoropropane to tetrafluoroethylene.

The reduction in the invention can use many conventional reduction methods such as a method to UV irradiate under a proton source, a method to apply zinc, a method to use hydrogen under a catalyst, and a method to employ potassium acetate and alcohol.

For UV irradiation reduction, alcohols such as methanol, ethanol, n-propanol, isopropanol, n-butanol, and sec-butanol are preferably used as a proton source, and the secondary alcohol such as isopropanol and sec-butanol are further used preferably.

To capture hydrogen chloride produced with a progress of the reaction, alkalis when added in the reaction system causes smooth reaction.

Alkaline material is desirable to be weakly basic property such as potassium carbonate, sodium carbonate, calcium carbonate, potassium bicarbonate, and sodium bicarbonate. Or without adding these acid capturing agents, hydrogen chloride generated may be discharged outside the reaction system by only heating.

As a UV source, any source can be used if only emitting the light of wavelength not more than 400 nm, for example, a high pressure mercury light and a low pressure mercury light are desirable. The reaction temperature of reduction process under the UV irradiation ranges normally 0° to 100° C. and preferably 10° to 80° C., and the reaction pressure is not specifically defined but preferably within atmospheric pressure to 2 kg/cm$^2$G.

As a solvent used for reduction process with zinc, a proton generating source for the reaction process is preferable, some alcohols such as methanol, ethanol, isopropanol, ethyleneglycol, and propyleneglycol are preferable. Zinc is preferable to be powder or particle, zinc powder is the best choice. The amount of zinc used may be not less than an equivalent mole for chlorine to be reduced or not less than 2 molar equivalent for the initial raw material.

The reduction process with zinc is done normally ranging room temperature to 120° C., preferably 40° to 100° C.. The reaction pressure is not specifically defined, but a range of atmospheric pressure to 8 kg/cm$^2$G is preferable.

Reduction using hydrogen under catalyst can apply both gaseous and liquid phase reactions. The reduction catalyst may use either noble metal catalysts such as platinum, palladium, rhodium, ruthenium, or hydrogenated catalysts such as Raney nickel, but the noble metal catalyst is used especially preferably. A carrier for the reducing catalyst uses preferably, for example, alumina and charcoal, especially alumina when used as a carrier increases the selectivity of the target. As a carrying method, a conventional preparation method of noble metal catalysts can be applied. It is desirable to reduce the catalyst before use to obtain a stable catalyst activity, but not always to need.

A ratio of hydrogen and initial raw material can be largely varied. Normally, chlorine atoms are hydrogenated using hydrogen at least stoichiometric amount, but considerably more quantities of hydrogen, for example, four equivalent or more to the initial raw material may be used to raise the conversion of the raw material and the selectivity of the target compound. For gaseous reaction, the suitable temperature is 80° to 350° C., preferably ranges particularly 100° to 200° C. A contacting time is 0.1 to 200 seconds, preferably particularly 1 to 60 seconds.

The liquid phase reduction may be carried out without solvent or with solvents such as alcohols including methanol, ethanol, and isopropanol, or ethers including tetrahydrofuran, dioxane, ethyleneglycoldimethylether, and acetic acid and pyridine. Hydrogen chloride generated with reaction process often lowers the catalyst activity and so some alkalis such as sodium hydroxide, potassium hydroxide, calcium hydroxide, soda lime, and aqueous ammonia may be added in the reaction system to capture the generated acid. The reaction temperature for the liquid phase is preferably usually at ~150° C., and the reaction pressure is preferably atmospheric pressure to 100 kg/cm$^2$G.

Solvent used during reduction by potassium acetate and alcohol is preferably to act as a proton source and is desirably alcohol such as methanol, ethanol, isopropanol, ethyleneglycol, or propyleneglycol, especially isopropanol. The amount of potassium acetate is sufficient to be an equivalent mole or more to chlorine atoms to be reduced or two molar equivalent or more to the initial raw material. The reaction is normally at room temperature to 120° C., preferably at 40° to 100° C., and the reaction pressure is not specifically defined but preferably ranges atmospheric pressure to 8 kg/cm$^2$G.

APPLICABILITY TO THE INDUSTRY

The present invention can provide new 2,2-dichloro-1,1,1,3,3,4,4,5,5,5-decafluoropentane and 3,3-dichloro-1,1,1,2,2,4,4,5,5,5-decafluoropentane as a precursor of alternatives of refrigerants, etc, at high yield and high selectivity. It is also economical because continuous reaction is available.

According to the present invention, HFC-43-10 mcf can be produced at high yield by reducing 3,3-dichloro-1,1,1,2,2,4,4,5,5,5-decafluoropentane.

EMBODIMENT

The present invention is described with some embodiments as follows.

Embodiment 1

Ten grams of aluminum chloride anhydride and 50 grams of trichlorofluoromethane were charged in an autoclave of 500 ml. After stirring for 3 hours at room temperature, unreacted trichlorofluoromethane and carbon tetrachloride generated therefrom, dichlorofluoromethane, and trifluorochloromethane were removed under reduced pressure.

A still of the autoclave was cooled to −20° C. and added by 100 grams of difluorodchloromethane. As stirring, 170 grams of tetrafluoroethylene was charged for about two hours, and continued to stir for about 5 hours. The content was taken out and the product was analyzed with a gas chromatography. Results are as follows.

The conversion of difluorodichloromethane and tetrafluoroethylene: 100% Product and its composition ratio (GC %): Heptafluorochloropropane: 2 Dichloropentafluoropropane: 10 Dichlorodecafluoropentane: 80 Pentafluorodichloropropane: 2 Hexafluorotrichloropentane: 8

Among the products, dichlorodecafluoropentane was a mixture of 90% of 3,3-dichloro-1,1,1,2,2,4,4,5,5,5-decafluoropentane and 10% of 2,2-dichloro-1,1,1,3,3,4,4,5,5,5-decafluoropentane. Both products have a boiling point of about 91° C. and are difficult to separate each other, but they were identified using $^{19}$F-NMR as follows.

$^{19}$F-NMR shows a chemical shift and an integral intensity, etc. referring to CFC-11.

| CF3<br>1 | CF2<br>2 | CCl2<br>2 | CF2<br>2 | CF3<br>1 | |
|---|---|---|---|---|---|
| Band | | Chemical shift (ppm) | | Integral intensity | Coupling |
| 1 | | −77.1 | | 6 | s |
| 2 | | −113.3 | | 4 | s |

| CF3<br>1 | CF2<br>2 | CCl2<br>3 | CF2<br>4 | CF3 | |
|---|---|---|---|---|---|
| Band | | Chemical shift (ppm) | | Integral intensity | Coupling |
| 1 | | −74.6 | | 3 | m |
| 2 | | −111.0 | | 2 | m |
| 3 | | −122.2 | | 2 | m |
| 4 | | −81.7 | | 3 | t J = 11.8 Hz |

Embodiment 2 (Applying UV-ray reduction)

In a quartz made photochemical reaction vessel of with a cooler, 32.1 grams of 3,3-dichloro-1,1,1,2,2,4,4,5,5,5-decafluoropentane, 21.2 grams of sodium carbonate and 300 ml of isopropanol were charged. After replacing atmosphere in the system with nitrogen gas, the content was stirred irradiating the inside of the reaction vessel using a high pressure mercury light keeping the reaction temperature at 25° C. to 30° C. to continue the reaction for about four hours.

The reaction mixture was analyzed using the gas chromatography to find that a conversion of raw material was 100% and HFC-43-10 mcf (1,1,1,2,2,4,4,5,5,5-decafluoropentane) was produced at 93% selectivity.

Embodiment 3 (use of zinc)

In a glass made reaction vessel of 300 ml with a cooler and a dropping funnel, 14.5 grams of zinc power and 100 ml of ethanol were charged. The content was refluxed by heating with stirring, 17.8 grams of 3,3-dichloro-1,1,1,2,2, 4,4,5,5,5-decafluoropentane was added from the dropping funnel for one hour and continued to react for another one hour refluxing by heating.

The reaction mixture, after cooled, was analyzed by the gas chromatography to show that the conversion of raw material was 100% and HFC-43-10 mcf was produced at 87% selectivity.

Embodiment 4 (applying catalytic reduction with hydrogen in gas phase)

In a Hastelloy C made reaction tube with an inner diameter of 20 mm, 40 ml of 0.5% palladium catalyst on alumina was charged. After passing hydrogen at flow rate of 80 cc/min. at 200° C. for two hours, at the reaction temperature of 200° C. a mixture of 3,3-dichloro- 1,1,1,2,2,4, 4,5,5,5-deafluoropentane and 2,2-dichloro- 1,1,1,3,3,4,4,5, 5,5-decafluoropentane with a ratio of 90 to 10 at the flow rate of 40 cc/min. and hydrogen at 100 cc/min. were passed in the tube to react.

Discharged gas from the reaction tube, after removing its acid component, was recovered at a cold trap at −78° C. and analyzed by the gas chromatography to find that the conversion of raw material was 95% and the target material, HFC-43-10 mcf, was produced at 88% selectivity and 1,1, 1,3,3,4,4,5,5,5-decafluoropentane was at 9% selectivity.

Embodiment 5 (applying liquid phase reduction with hydrogen)

In a 300 ml stainless steel SUS 316 made autoclave, 150 ml of ethyleneglycoldimethylether, 16.8 grams of potassium hydroxide and 32 grams of 3,3-dichloro-1,1,1,2,2,4,4,5,5,5-decafluoropentane were charged. After pressure-reducing the system, hydrogen was charged to 20 kg/cm$^2$G, then it was heated to 100° C. with stirring and hydrogen consumed by reaction was continuously added to continue to the extent not to consume hydrogen.

After cooled, the reaction mixture was analyzed using the gas chromatography to find that the conversion of raw material was 100% and the target HFC-43-10 mcf was produced at 82% selectivity.

Embodiment 6 (use of potassium acetate)

In a glass made reaction vessel of 300 ml with a cooler and a dropping funnel, 21.8 grams of potassium acetate and 100 ml of isopropanol were charged. The content was refluxed by heating with stirring, and 17.8 grams of 3,3-dichloro-1,1,1,2,2,4,4,5,5,5-decafluoropentane was added from dropping funnel for one hour and then the reaction was continued refluxing by heating for additional one hour. After cooled, the reaction mixture was analyzed using the gas chromatography to show that the conversion of raw material was 100% and HFC-43-10 mcf was produced at 90% selectivity.

What is claimed is:

1. A method for preparing 3,3-dichloro-1,1,1,2,2,4,4, 5,5,5-decafluoropentane which comprises reacting two moles of tetrafluoroethylene with one mole of difluorodichloromethane in the presence of a Lewis acid catalyst selected from the group consisting of aluminum chloride anhydride, tin tetrachloride anhydride, antimony pentachloride anhydride, zinc chloride anhydride, iron chloride anhydride, boron trifluoride, and chlorofluorides of the formula AlClxFy, ZrClpFq, TiClpFq wherein x+y=3, 0<x<3, 0<y<3, p+q=4, 0<p<4, and 0<q<4.

2. A method according to claim 1, wherein the Lewis acid catalyst is contacted with the tetrafluoroethylene and the difluorodichloromethane in a gaseous or liquid phase at a temperature of −20° to 100° C.

3. A method for preparing 1,1,1,2,2,4,4,5,5,5-decafluoropentane which comprises reacting two moles of tetrafluoroethylene with one mole of difluorodichloromethane in the presence of a Lewis acid catalyst selected from the group consisting of aluminum chloride anhydride, tin tetrachloride anhydride, antimony pentachloride anhydride, zinc chloride anhydride, iron chloride anhydride, boron trifluoride, and chlorofluorides of the formula AlClxFy, ZrClpFq, or TiClpFq wherein x+y=3, 0<x<3, 0<y<3, p+q=4, 0<p<4, and 0<q<4, to form 3,3-dichloro-1,1,1,2,2,4,4,5,5,5-decafluoropentane; and reducing the 3,3-dichloro-1,1,1,2,2, 4,4,5,5,5-decafluoropentane to 1,1,1,2,2,4,4,5,5,5-decafluoropentane.

4. The method according to claim 3, wherein the dichlorodecafluoropropane is reduced by reaction with protons in the presence of ultraviolet light having a wavelength of 400 nm or less at a temperature of from 0° to 100° C.

5. The method according to claim 3, wherein the dichlorodecafluoropentane is reduced by reaction with zinc at a temperature of from room temperature to 120° C.

6. The method according to claim 3, wherein the dichlorodecafluoropentane is reduced by reaction with hydrogen in the presence of a catalyst for hydrogenation at a temperature of from room temperature to 350° C.

7. The method according to claim 3, wherein the dichlorodecafluoropetane is reduced by reaction with potassium acetate and alcohol at a temperature of from room temperature to 120° C.

* * * * *